United States Patent
Na et al.

(10) Patent No.: US 10,383,844 B2
(45) Date of Patent: Aug. 20, 2019

(54) METHODS FOR TREATING PULMONARY FIBROSIS USING CHROMENONE DERIVATIVES

(71) Applicants: College of Medicine Pochon Cha University Industry—Academic Cooperation Foundation, Gyeonggi-do (KR); EWHA University—Industry Collaboration Foundation, Seoul (KR); Industry—Academic Cooperation Foundation, Yonsei University, Seoul (KR)

(72) Inventors: Younghwa Na, Seoul (KR); Yun-Sil Lee, Seoul (KR); Jae Ho Cho, Seoul (KR)

(73) Assignees: College of Medicine Pochon Cha University Industry—Academic Cooperation, Gyeonggi-Do (KR); EWHA University—Industry Collaboration Foundation, Seoul (KR); Industry-Academic Cooperation Foundation, Yonsei University, Seoul (KR)

( * ) Notice: Subject to any disclaimer, the term of this patent is extended or adjusted under 35 U.S.C. 154(b) by 0 days.

(21) Appl. No.: 15/986,033

(22) Filed: May 22, 2018

(65) Prior Publication Data
US 2018/0338948 A1 Nov. 29, 2018

(30) Foreign Application Priority Data
May 23, 2017 (KR) .......................... 10-2017-0063643

(51) Int. Cl.
*A61K 31/353* (2006.01)
*A61K 31/38* (2006.01)
*A61P 11/00* (2006.01)

(52) U.S. Cl.
CPC ............ *A61K 31/353* (2013.01); *A61K 31/38* (2013.01); *A61P 11/00* (2018.01)

(58) Field of Classification Search
CPC .............................. A61K 31/353; A61K 31/38
See application file for complete search history.

(56) References Cited

U.S. PATENT DOCUMENTS

2010/0093613 A1* 4/2010 Kunkel .............. G01N 33/5055
 514/1.1
2012/0029071 A1* 2/2012 Biswal .................. A61K 31/00
 514/527

FOREIGN PATENT DOCUMENTS

| CN | 1493571 A | * 5/2004 |
| KR | 10-2013-0084987 A | 7/2013 |
| KR | 10-2014-0037954 A | 3/2014 |

OTHER PUBLICATIONS

CN1493571A, Abstract English translation (2004) (Year: 2004).*

* cited by examiner

*Primary Examiner* — Yong L Chu
(74) *Attorney, Agent, or Firm* — Fish & Richardson P.C.

(57) ABSTRACT

A composition for prevention or treatment of pulmonary fibrosis comprising chromenone derivatives represented by Formula I of the present invention or pharmaceutically acceptable salts thereof as an active ingredient, produces altered heat shock protein 27 (HSP27) dimers, thereby preventing normal HSP27 non-phosphorylated polymers from performing a chaperone function and reducing a cell protection function that chaperone originally performs. Thus the inventive composition has a remarkable inhibitory effect on pulmonary fibrosis, in particular, an irradiation-induced pulmonary fibrosis phenomenon.

5 Claims, 3 Drawing Sheets

[A]

[B]

[C]

METHODS FOR TREATING PULMONARY FIBROSIS USING CHROMENONE DERIVATIVES

TECHNICAL FIELD

The present invention relates to a method for treating pulmonary fibrosis comprising administering a therapeutically effective amount of chromenone derivatives or pharmaceutically acceptable salts thereof to a patient. Particularly, the present invention relates to a method for treating pulmonary fibrosis resulting from radiation treatment, comprising administering a therapeutically effective amount of chromenone derivatives having a heat shock protein 27 (HSP27) inhibitory activity or pharmaceutically acceptable salts thereof.

BACKGROUND

Pulmonary fibrosis or idiopathic pulmonary fibrosis (IPF) is a disease of unknown cause, characterized by chronically progressive fibrosis of mesopulmonum. The occurrence of the above disease is mainly limited to lungs, showing signs of a histologically pathognomonic usual interstitial pneumonia (UIP). A prevalence rate of pulmonary fibrosis varies among reports, but is known to be 2-29 people per 100,000 of the population and is designated as a rare incurable disease in South Korea. Clinical outcomes of the IPF vary widely, wherein the IPF is a critical disease which generally progresses into a respiratory failure due to a slowly progressive pulmonary function insufficiency and in which an average time of survival after diagnosis is within 2-3 years. For that reason, many attempts have been made to find an exact cause and etiological factor of the IPF and develop a medicine accordingly, but there has been no proper medicine so far.

Also, radiation treatment is one of the main treatment modalities in lung cancer, contributing to both its cure and palliation in localized and advanced disease, respectively. However, about 70-80% of all the lung cancer patients who receive the radiation treatment suffer from mild or severe side effects on their lung organs. Pulmonary fibrosis, one of the representative side effects resulting from the radiation treatment, brings about a functional loss of lung organs and reduces a lung capacity of patients, thus having a negative effect on their quality of life and leading to even death. However, due to a lack of effective drugs to prevent or reduce a state of such disease, both pneumonia and pulmonary fibrosis caused after irradiating lungs are a serious problem that have to be urgently solved.

In particular, for the pulmonary fibrosis resulting from the existing radiation treatment, efforts have been made to reduce its side effects only by administering steroid later upon the outbreak of radiation pneumonia, which occurs in its previous stage of fibrosis. However, there has been no substantial medicine for radiation-induced pulmonary fibrosis. Steroid therapy also has many side effects, thus having a limit on administration for a long period of time.

The heat shock protein 27 (HSP27) was originally known as a representative chaperone protein, promoting carcinogenesis as a low molecular weight chaperone protein and causing cancer resistance, but also has been recently known to be involved in a tissue fibrosis process.

Against this backdrop, it is urgent to find a medicine for pulmonary fibrosis, in particular, for radiation-induced pulmonary fibrosis.

PRIOR ART REFERENCES

Patent Documents

KR 10-2014-0037954 (Mar. 27, 2014)
KR 10-2013-0084987 (Jul. 26, 2013)

SUMMARY OF THE INVENTION

Technical Problem

The objective of the present invention is to provide a method for treating pulmonary fibrosis comprising administering a therapeutically effective amount of chromenone derivatives represented by Formula I or pharmaceutically acceptable salts thereof to a patient.

Technical Solution

The present inventors have found that chromenone derivatives represented by Formula I or pharmaceutically acceptable salts thereof show an effect on prevention or treatment of pulmonary fibrosis through a heat shock protein 27 (HSP27) inhibitory activity.

The present invention provides a method for treating pulmonary fibrosis comprising administering a therapeutically effective amount of chromenone derivatives represented by Formula I or pharmaceutically acceptable salts thereof to a patient.

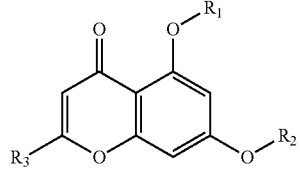

[Formula I]

In the above formula I, $R_1$ and $R_2$ are each independently hydrogen, or heterocyclic $C_{1-4}$ alkyl consisting of one or two heteroatoms selected from the group consisting of oxygen, nitrogen and sulfur, and one to six carbon atoms;

$R_3$ is $C_{1-10}$ alkyl, $C_{3-10}$ cycloalkyl, $C_{6-14}$ aryl, or heteroaryl consisting of one to four heteroatoms selected from the group consisting of oxygen, nitrogen and sulfur, and one to ten carbon atoms, wherein one or more hydrogen atoms of $R_3$ are each independently substituted or unsubstituted with $R_4$; and $R_4$ is F, Br, Cl, I, OH, OMe, OEt, $NH_2$, $NMe_2$, CN, COOH, COMe, COOMe, $CONH_2$ or $C_{1-4}$ alkyl.

According to a preferred embodiment aspect of the present invention, in the above formula I, $R_1$ and $R_2$ are each independently hydrogen,

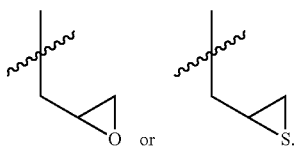 [SMILES: *CC1CO1 ; *CC1CS1]

or

According to a preferred embodiment aspect of the present invention, in the above formula I, $R_3$ is $C_{1-10}$ alkyl or $C_{3-10}$ cycloalkyl.

According to a more preferred embodiment aspect of the present invention, in the above formula I, $R_3$ is methyl or phenyl.

Also, according to another preferred embodiment aspect of the present invention, a compound of the above formula I may be selected from the group consisting of compounds of a following table 1.

TABLE 1

| Compound | Structure |
|---|---|
| 1 | 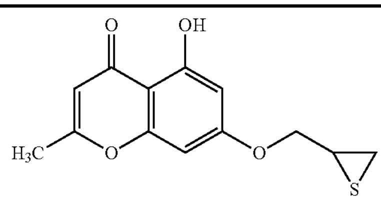 |
| 2 | 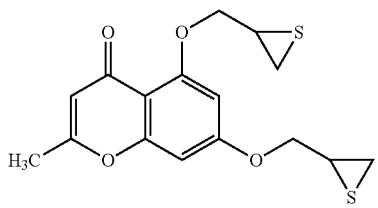 [SMILES: Cc1cc(=O)c2c(OCC3CS3)cc(OCC3CS3)cc2o1] |
| 3 | 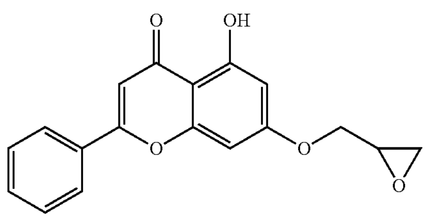 [SMILES: O=c1cc(-c2ccccc2)oc2cc(OCC3CO3)cc(O)c12] |
| 4 | 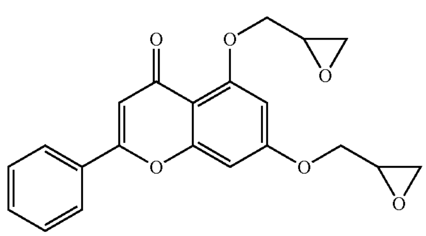 [SMILES: O=c1cc(-c2ccccc2)oc2cc(OCC3CO3)cc(OCC3CO3)c12] |
| 5 | 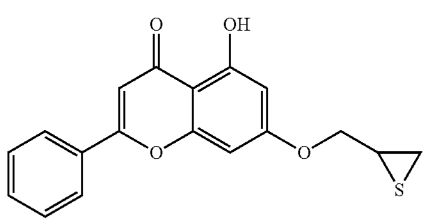 [SMILES: O=c1cc(-c2ccccc2)oc2cc(OCC3CS3)cc(O)c12] |
| 6 | 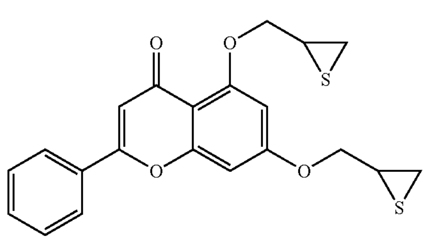 [SMILES: O=c1cc(-c2ccccc2)oc2cc(OCC3CS3)cc(OCC3CS3)c12] |

In the present invention, pharmaceutically acceptable salts mean the salts conventionally used in a pharmaceutical industry, and are, for example, inorganic ion salts prepared from calcium, potassium, sodium, magnesium and the like; inorganic acid salts prepared from hydrochloric acid, nitric acid, phosphoric acid, bromic acid, iodic acid, perchloric acid, tartaric acid, sulfuric acid and the like; organic acid salts prepared from acetic acid, trifluoroacetic acid, citric acid, maleic acid, succinic acid, oxalic acid, benzoic acid, tartaric acid, fumaric acid, mandelic acid, propionic acid, lactic acid, glycolic acid, gluconic acid, galacturonic acid, glutamic acid, glutaric acid, glucuronic acid, aspartic acid, ascorbic acid, carbonic acid, vanillic acid, hydroiodic acid, etc.; sulfonic acid salts prepared from methane sulfonic acid, ethane sulfonic acid, benzene sulfonic acid, p-toluenesulfonic acid, naphthalenesulfonic acid and the like; amino acid salts prepared from glycine, arginine, lysine, etc.; amine salts prepared from trimethylamine, triethylamine, ammonia, pyridine, picoline, etc.; and the like, but types of salts meant in the present invention are not limited by the above-listed salts.

According to the present invention, the above pulmonary fibrosis may include idiopathic pulmonary fibrosis, pulmonary fibrosis resulting from anticancer therapy, middle east respiratory syndrome (MERS) or pneumonia, but is not limited thereto.

According to a preferred embodiment aspect of the present invention, the anticancer therapy is radiotherapy.

A composition according to the present invention including chromenone derivatives represented by Formula I or pharmaceutically acceptable salts induces a production of modified HSP27 dimers and inhibits a production of HSP27 giant polymers, thereby having an effect of inhibiting a chaperone function of the HSP27 and reducing a cell protection function thereof.

The composition according to the present invention may contain 0.01 to 99 wt %, preferably 0.1 to 30 wt % of the compound of Formula I with regard to a total weight of the composition.

The composition according to the present invention may further include pharmaceutically acceptable additives, wherein the pharmaceutically acceptable additives may be, for example, starch, gelatinized starch, microcrystalline cellulose, milk sugar, povidone, colloidal silicon dioxide, calcium hydrogen phosphate, lactose, mannitol, crude maltose, arabic gum, pregelatinized starch, maize starch, powdered cellulose, hydroxypropyl cellulose, opadry, sodium starch glycolate, carnauba wax, synthetic aluminum silicate, stearic acid, magnesium stearate, aluminum stearate, calcium stearate, white sugar, dextrose, sorbitol, talc and the like, but are not limited thereto.

The pharmaceutically acceptable additives according to the present invention are contained in an amount of 1 to 50 parts by weight, preferably 20 to 50 parts by weight, with regard to 100 parts by weight of the pharmaceutical composition for prevention or treatment of pulmonary fibrosis comprising chromenone derivatives represented by the above formula I or pharmaceutically acceptable salts thereof as active ingredients, but are not limited thereto.

In other words, the composition of the present invention may be administered in various oral and parenteral formulations during its actual clinical administration. In case of being formulated into preparations, the composition of the present invention may be prepared by using diluents or excipients such as fillers, extenders, binders, humectants, disintegrants, surfactants, etc., which are commonly used. Solid preparations for oral administration may include tablets, pills, powder, granules, capsules, etc., wherein such solid preparations may be prepared by mixing the composition with at least one excipient, for example, starch, calcium carbonate, sucrose, lactose, gelatin or the like. Besides simple excipients, such preparations may also use lubricants such as magnesium stearate and talc. Liquid preparations for oral administration correspond to suspending agents, liquid for internal use, emulsion, syrup and the like. Besides water and liquid paraffin, which are commonly used simple diluents, such preparations may include various excipients, for example, humectants, sweetening agents, air fresheners, preservatives, etc. Preparations for parenteral administration may include sterilized aqueous solution, non-aqueous solvent, suspending agents, emulsion, freeze-dried preparations and suppositories. Non-aqueous solvents and suspending agents may be vegetable oils such as propylene glycol, polyethylene glycol and olive oil, an injectable ester such as ethyl oleate, etc. Suppository bases may be witepsol, macrogol, tween 61, cacao butter, laurinum, glycerogelatin, etc.

The composition of the present invention may be orally or parenterally administered according to purposes. As for the parenteral administration, it is preferable to select an external application on skin or an intraperitoneal injection, an intrarectal injection, a hypodermic injection, an intravenous injection, an intramuscular injection or an intrathoracic injection. The range of dosages varies depending on a patient's weight, age, gender, health condition, diet, administration time, administration method, excretion rate, disease severity and the like.

As for the composition of the present invention, the range of dosages varies depending on a patient's weight, age, gender, health condition, diet, administration time, administration method, excretion rate, disease severity and the like, and a daily dosage is 0.01 to 1000 mg/kg, preferably 1 to 30 mg/kg based on the amount of the inventive composition, which can be administered 1 to 6 times a day or once in several days.

Advantageous Effects

A pharmaceutical composition for prevention or treatment of pulmonary fibrosis comprising chromenone derivatives represented by Formula 1 of the present invention or pharmaceutically acceptable salts thereof as an active ingredient produces modified heat shock protein 27 (HSP27) dimers, thereby preventing normal HSP27 non-phosphorylated polymers from performing a chaperone function and reducing a cell protection function that chaperone originally performs, such that the inventive composition has a remarkable effect of inhibiting pulmonary fibrosis, in particular, a pulmonary fibrosis phenomenon resulting from radiation treatment.

MODE FOR INVENTION

Figure 1:
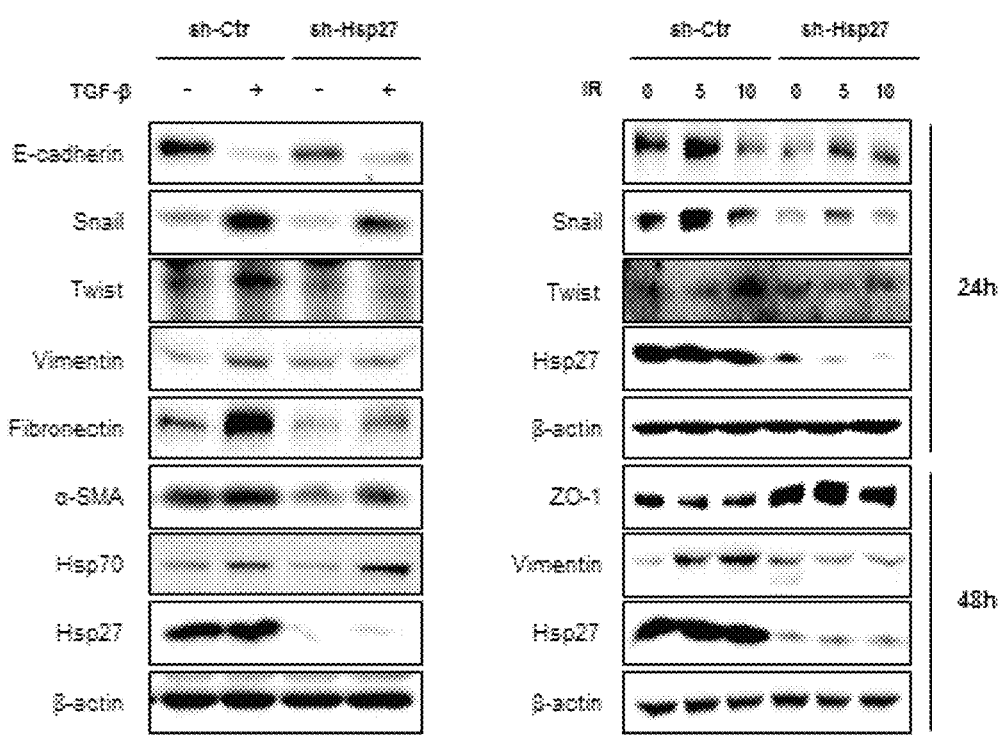
FIG. 1 shows results of identifying a difference in degrees of Epithelial to Mesenchymal Transition (EMT), a process of pulmonary fibrosis, in L132 cells according to the presence or absence of HSP27, by means of western blots.

Hereinafter, preferred Examples will be suggested for better understanding of the present invention. However, the following Examples are provided only for the purpose of illustrating the present invention, and thus the present invention is not limited thereto.

Example 1: Preparing of 5-hydroxy-2-methyl-7-(thiirane-2-ylmethoxy)-4H-chromene-4-one (Compound 1) and 2-methyl-5,7-bis(thiirane-2-ylmethoxy)-4H-chromene-4-one (Compound 2)

Epithiochlorohydrin (1.13 g, 10.40 mmol) was added to a reaction mixture of 5,7-dihydroxy-2-methyl-4H-chromene-4-one (0.50 g, 2.60 mmol) and $K_2CO_3$ (0.72 g, 5.20 mmol) in a DMF/acetone (20 mL/10 mL) and then the reaction mixture was stirred at 90° C. for 21 h. After cooling the reaction mixture to room temperature, water was added and the reaction mixture was extracted with ethyl acetate. Organic layer was collected and washed with water and brine, which was dried over anhydrous $MgSO_4$. Solvent was removed under reduced pressure and the residue was purified on a silica gel column chromatography (eluent: $CH_2Cl_2 \rightarrow$ ethyl acetate:n-hexane=1:1) to obtain a compound 1 (ivory-colored solid, 0.32 g, 46.8%) and a compound 2 (orange-colored solid, 0.08 g, 8.7%).

Compound 1: $R_f$ 0.36 (ethyl acetate:n-hexane=1:3); mp: 152-153° C.; HPLC: $R_T$ 5.91 min (purity: 99.39%); $^1$H-NMR (CDCl$_3$, 400 MHz) δ 2.33 (dd, J=6.8, 1.2 Hz, 1H), 2.34 (s, 3H), 2.63 (dd, J=6.4, 0.8 Hz, 1H), 3.24-3.30 (m, 1H), 3.97 (dd, J=10.0, 2.4 Hz, 1H), 4.21 (dd, J=10.4, 1.2 Hz, 1H), 6.03 (s, 1H), 6.33 (d, J=2.4 Hz, 1H), 6.35 (d, J=2.4 Hz, 1H), 12.70 (s, 1H); $^{13}$C-NMR (CDCl$_3$, 100 MHz) 20.7, 24.0, 31.0, 73.1, 93.2, 98.6, 105.7, 109.1, 158.3, 162.5, 164.1, 167.1, 182.7 ppm.

Compound 2: $R_f$ 0.14 (ethyl acetate:n-hexane=1:1); mp: 95-96° C.; HPLC: $R_T$ 4.77 min (purity: 99.0%); $^1$H-NMR (CDCl$_3$, 400 MHz) δ 2.27 (s, 3H), 2.34 (dd, J=5.6, 1.6 Hz, 1H), 2.48 (dd, J=5.2, 0.8 Hz, 1H), 2.63-2.66 (m, 2H), 3.24-3.30 (m, 1H), 3.38-3.44 (m, 1H), 3.91 (dd, J=10.0, 7.2 Hz, 1H), 3.99 (dd, J=10.0, 6.8 Hz, 1H), 4.21 (dd, J=10.0, 5.6 Hz, 1H), 4.39 (dd, J=10.0, 4.8 Hz, 1H), 6.00 (d, J=0.8 Hz, 1H), 6.37 (d, J=2.4 Hz, 1H), 6.43 (d, J=2.4 Hz, 1H); $^{13}$C-NMR (CDCl$_3$, 100 MHz) 20.0, 23.9, 24.6, 30.9, 31.1, 73.1, 74.2, 94.5, 98.8, 109.9, 112.2, 159.9, 160.2, 162.4, 163.4, 177.4 ppm.

Example 2: Preparing of 5-hydroxy-7-(oxirane-2-ylmethoxy)-2-phenyl-4H-chromene-4-one (Compound 3) and 5,7-bis(oxirane-2-ylmethoxy)-2-phenyl-4H-chromene-4-one (Compound 4)

Epichlorohydrin (1.82 g, 19.65 mmol) was added to a reaction mixture of 5,7-dihydroxyflavone (1.00 g, 3.93 mmol) and $K_2CO_3$ (1.09 g, 7.86 mmol) in a DMF/acetone (12 mL/4 mL) and then the reaction mixture was stirred at 90° C. for 20 h. After cooling the reaction mixture to room temperature, water was added and the reaction mixture was extracted with ethyl acetate. Organic layer was collected and washed with water and brine, which was dried over anhydrous $MgSO_4$. Solvent was removed under reduced pressure and the residue was purified on a silica gel column chromatography (eluent:MeOH:CHCl$_3$=3:97→4:96) to obtain a compound 3 (ivory-colored solid, 0.07 g, 5.7%) and a compound 4 (ivory-colored solid, 0.30 g, 20.8%).

Compound 3: R$_f$ 0.24 (ethyl acetate:n-hexane=1:3); HPLC: R$_T$ 5.67 min (purity: 100%); $^1$H-NMR (CDCl$_3$, 400 MHz) δ2.79 (dd, J=4.4, 2.4 Hz, 1H), 2.95 (dd, J=4.4, 4.0 Hz, 1H), 3.37-3.41 (m, 1H), 4.00 (dd, J=11.2, 6.0 Hz, 1H), 4.34 (dd, J=11.2, 2.8 Hz, 1H), 6.39 (d, J=2.4 Hz, 1H), 6.54 (d, J=2.4 Hz, 1H), 6.68 (s, 1H), 7.51-7.56 (m, 3H), 7.87-790 (m, 2H), 12.73 (s, 1H); $^{13}$C-NMR (CDCl$_3$, 100 MHz) 44.6, 49.7, 69.2, 93.3, 98.6, 105.9, 106.0, 126.3, 129.1, 131.3, 131.9, 157.8, 162.3, 164.1, 164.3, 182.5 ppm; HRMS-ESI (m/z) [M-H]$^-$ C$_{18}$H$_{15}$O$_5$ calcd 311.0914, found 311.0918.

Compound 4: R$_f$ 0.39 (MeOH:CHCl$_3$=1:24); HPLC: R$_T$ 7.72 min (purity: 98.89%); $^1$H-NMR (CDCl$_3$, 400 MHz) δ 2.80 (dd, J=4.8, 2.8 Hz, 1H), 2.95-2.97 (m, 2H), 3.14-3.16 (m, 1H), 3.38-3.43 (m, 1H), 3.44-3.48 (m, 1H), 6.50 (d, J=2.4 Hz, 1H), 6.61 (d, J=2.4 Hz, 1H), 6.64 (s, 1H), 7.48-7.52 (m, 3H), 7.85-788 (m, 2H); $^{13}$C-NMR (CDCl$_3$, 100 MHz) 44.6, 45.0, 49.8, 50.2, 69.2, 69.3, 94.5, 98.3, 109.1, 110.0, 126.0, 129.0, 131.3, 131.5, 159.7, 159.8, 160.8, 162.6, 177.2 ppm; HRMS-ESI (m/z) [M-H]$^-$ C$_{21}$H$_{19}$O$_6$ calcd 367.1176, found 367.1183.

Example 3: Preparing of 5-hydroxy-2-phenyl-7-(thiirane-2-ylmethoxy)-4H-chromene-4-one (Compound 5) and 2-phenyl-5,7-bis(thiirane-2-yl-methoxy)-4H-chromene-4-one (Compound 6)

Epichlorohydrin (0.64 g, 5.91 mmol) was added to a reaction mixture of 5,7-dihydroxyflavone (0.50 g, 1.97 mmol) and Cs$_2$CO$_3$ (1.28 g, 3.93 mmol) in a DMF/acetone (5 mL/15 mL) r and then the reaction mixture was stirred at 80° C. for 20 h. After cooling the reaction mixture to room temperature, water was added and the reaction mixture was extracted with ethyl acetate. Organic layer was collected and washed with water and brine, which was dried over anhydrous MgSO$_4$. Solvent was removed under reduced pressure and the residue was purified on a silica gel column chromatography (eluent: CH$_2$Cl$_2$→ethyl acetate:n-hexane=2:1) to obtain a compound 5 (yellow-colored solid, 0.05 g, 8.0%) and a compound 6 (yellow-colored solid, 0.08 g, 8.9%).

Compound 5: R$_f$ 0.47 (ethyl acetate:n-hexane=1:3); HPLC: R$_T$ 8.30 min (purity: 98.56%); $^1$H-NMR (CDCl$_3$, 400 MHz) δ 2.36 (dd, J=5.2, 1.2 Hz, 1H), 2.65 (dd, J=6.4, 1.2 Hz, 1H), 3.27-3.33 (m, 1H), 4.00 (dd, J=10.4, 6.8 Hz, 1H), 4.26 (dd, J=10.0, 5.2 Hz, 1H), 6.38 (d, J=2.0 Hz, 1H), 6.51 (d, J=2.0 Hz, 1H), 6.68 (s, 1H), 7.50-7.56 (m, 3H), 7.87-790 (m, 2H), 12.73 (s, 1H); $^{13}$C-NMR (CDCl$_3$, 100 MHz) 23.8, 30.7, 73.0, 93.2, 98.7, 106.0, 126.3, 129.1, 131.3, 131.9, 157.8, 162.3, 164.1, 164.2, 182.5 ppm; $^{13}$C-NMR (CDCl$_3$, 100 MHz) 44.9, 50.2, 69.3, 112.8, 113.2, 115.6, 121.7, 124.8, 129.6, 129.8, 130.8, 133.1, 145.0, 152.0, 157.2, 192.2 ppm; HRMS-ESI (m/z) [M-H]$^-$ C$_{18}$H$_{15}$O$_4$S calcd 327.0686, found 327.0688.

Compound 6: R$_f$ 0.22 (ethyl acetate:n-hexane=1:1); HPLC: R$_T$ 6.23 min (purity: 97.82%); $^1$H-NMR (CDCl$_3$, 400 MHz) δ 2.36 (dd, J=5.2, 1.2 Hz, 1H), 2.51 (dd, J=5.2, 1.6 Hz, 1H), 2.64-2.69 (m, 2H), 3.27-3.33 (m, 1H), 3.41-3.47 (m, 1H), 3.95 (dd, J=10.4, 3.2 Hz, 1H), 4.04 (dd, J=10.4, 3.2 Hz, 1H), 4.25 (dd, J=10.0, 5.6 Hz, 1H), 4.43 (dd, J=10.4, 4.8 Hz, 1H), 6.42 (d, J=2.4 Hz, 1H), 6.59 (d, J=2.4 Hz, 1H), 6.64 (s, 1H), 7.48-7.52 (m, 3H), 7.84-787 (m, 2H); $^{13}$C-NMR (CDCl$_3$, 100 MHz) 23.8, 30.7, 73.0, 93.2, 98.7, 106.0, 126.3, 129.1, 131.3, 131.9, 157.8, 162.3, 164.1, 164.2, 182.5 ppm; $^{13}$C-NMR (CDCl$_3$, 100 MHz) 23.7, 24.4, 30.7, 31.0, 73.0, 74.0, 94.5, 98.8, 109.1, 110.1, 126.0, 129.0, 131.3, 131.5, 159.7, 160.8, 162.5, 177.2 ppm; HRMS-ESI (m/z) [M-H]$^-$ C$_{21}$H$_{19}$O$_4$S$_2$ calcd 399.0719, found 399.0723.

EXPERIMENTAL EXAMPLE

Experimental Example 1: Identifying of a Difference in Degrees of Epithelial to Mesenchymal Transition (EMT) According to the Presence or Absence of HSP27

A following experiment was performed to identify if HSP27 is an essential factor for Epithelial to Mesenchymal Transition (EMT), a process of pulmonary fibrosis.

For the experiment, L132 cells were cultured at 37° C. in a 5% CO$_2$ incubator by using an RPMI 1640 (RPMI, GIBCO-Invitrogen, Paisley, Scotland, UK) medium containing 10% FBS and 1× Antibiotic-Antimycotic (GIBCO-Invitrogen, Paisley, Scotland, UK).

An expression of HSP27 was inhibited by using a small hairpin RNA of the HSP27 in the above-cultured L132 cells. The above cells were treated with 5 ng/ml of TGF-beta (Transforming Growth Factor-beta), known to induce the EMT, after which the resulting cells were identified in 48 hours later, such that the cells were treated with a radiation dose of 5 Gy and 10 Gy and identified with western blots in 24 and 48 hours later.

To carry out the western blots, the treated cells were respectively washed twice with 1×PBS (0.14 M NaCl, 2.68 mM KCl, 10 mM Na$_2$HPO$_4$, 1.83 mM KH$_2$PO$_4$), after which the resulting cells were dissolved in a protein lysis buffer (100 mM Tris-HCl (pH 7.5), 50 mM NaCl, 5 mM EDTA (pH 8.0), 0.5% NP-40, 0.5% Sodium deoxycholate, 50 mM β-glycerophosphate, 0.1 mM Na$_3$VO$_4$, 50 mM NaF). A cell suspension was centrifuged at 13000 rpm for 30 minutes, after which only a supernatant thereof was taken out, such that 1% BSA solution was injected by 8, 6, 4, 2 and 0 μL into Protein Dye 1 mL as a standard by using a Bradford assay and 2 μL of the supernatant was added thereinto. The resulting solution was divided by 200 μL into each of a 96-well plate, after which the resulting plate was put into an ELISA reader to measure an optical observance thereof at an wavelength of 595 nm, such that a 6× sample buffer (0.35 M Tris (pH 6.8), 3% glycerol, 1% Sodium Dodecyl Sulfate, 6 mM Dithiothreitol) was injected to make a sample containing the same amount of protein. Then, the resulting sample was soaked in 100° C. water and boiled for 5 minutes and the same amount of protein was analyzed by using SDS-PAGE. A primary antibody used for the western blots was anti-HSP27 and β-actin (Santacruz, sc-13132 and sc-47778), and also anti-E-cadherin (BD, #610181), anti-Vimentin (BD, #550513), anti-Fibronectin (BD, #610077), anti-snail (Cell signaling, #3895S), anti-alpha-smooth muscle actin (Sigma, A5228), and anti-Zo-1 (Life technologies, #402200) were used. A secondary antibody used was Goat anti rabbit and Goat anti mouse (Santacruz, sc-2004 and sc-2005).

In result, as shown in FIG. 1, HSP27 knock-downed cells showed an increased expression of epithelial cell markers such as E-cadherin and ZO-1, and an inhibited expression of mesenchymal cell markers such as Snail, Twist, Fibronectin, Vimentin and alpha-smooth muscle actin than a control group.

Thus, if the function of HSP27 was inhibited, it can be seen that an overall EMT phenomenon was decreased.

Experimental Example 2: Identifying of a Productivity of Altered HSP27 Dimers in Cells To identify a degree of productivity of altered HSP27 dimers in cells, L132, a normal lung cell, was treated with Compound 1 of the present invention at 0.05, 0.1, 0.5 and 10 µM concentrations, and the cell was treated with SW15 at a 10 µM concentration for 24 hours as a positive control group. Then, a cell culture and western blots were performed in the same method as the above Experimental Example 1.

Figure 2:
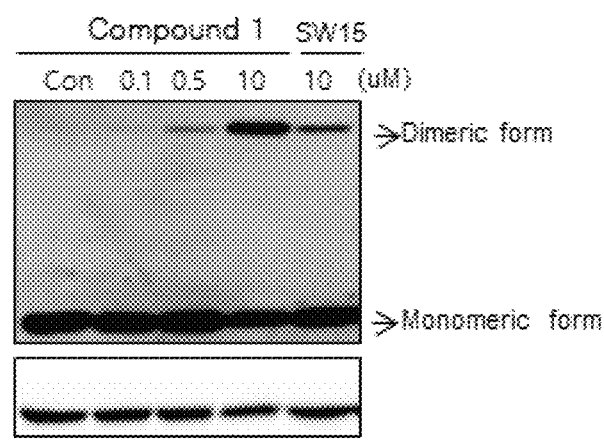
FIG. 2 shows results of identifying that a productivity of altered HSP27 dimers is increased in a concentration-dependent way, by means of western blots.

In result, as shown in FIG. 2, if the cell was treated with the compound of the present invention, it was identified that altered HSP27 dimers were increased in a dose-dependent manner, and normal HSP27 monomers were decreased at 10 µM that is a relatively high concentration.

Thus, it can be identified that the compound of the present invention has an effect on prevention or treatment of pulmonary fibrosis through an inhibition of HSP27 activity.

Experimental Example 3: Identifying of a Difference in Degrees of Epithelial to Mesenchymal Transition (EMT) According to Production of Altered HSP27 Dimers 3-1. Comparison of EMT Degrees by Means of TGF-Beta To identify a degree of EMT according to a production of altered HSP27 dimers in cells, L132, a normal lung cell, was treated with Compound 1 of the present invention at a 0.1 µM concentration, and in 1 hour later the cell was treated with TGF-beta at a 5 ng/mL concentration for 48 hours. Then, a cell culture and western blots were performed in the same method as the above Experimental Example 1.

Figure 3:
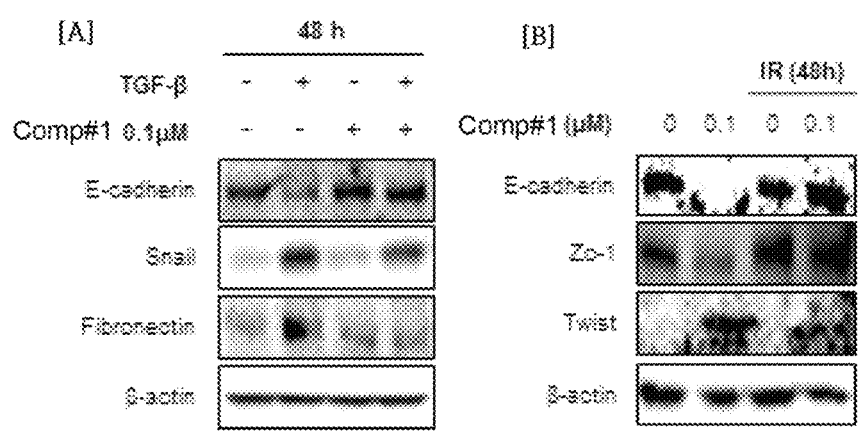
FIG. 3 shows results of identifying a difference in degrees of the EMT in L132 cells according to a production of altered HSP27 dimers, by means of western blots.

In result, as shown in FIG. 3(A), Compound 1 of the present invention specifically acts on HSP27, thus increasing altered HSP dimers in a dose-dependent manner, mitigating a decrease in an expression of E-cadherin, a marker of epithelial cells, and inhibiting an increase in an expression of Snail and Fibronectin, markers of mesenchymal cells.

Thus, it can be identified that the compound of the present invention has an effect on prevention or treatment of pulmonary fibrosis.

3-2. Comparison of EMT Degrees by Means of Radiation

To identify a relation between a degree of radiation-induced EMT and the inventive compound, L132, a normal lung cell, was treated with Compound 1 of the present invention at a 0.1 µM concentration, and in 1 hour later the resulting cell was exposed to a radiation dose of 5 Gy for 48 hours. Then, a cell culture and western blots were performed in the same method as the above Experimental Example 1.

In result, as shown in FIG. 3(B), Compound 1 of the present invention mitigated a decrease in an expression of E-cadherin and Zo-1 by means of radiation and inhibited an increase in an expression of Twist, a marker of mesenchymal cells.

Thus, it can be identified that the compound of the present invention has an effect on prevention or treatment of pulmonary fibrosis.

Experimental Example 4: Identifying of an Anti-Pulmonary Fibrosis Effect According to Production of Altered HSP27 Dimers in a Small Animal Model on Lung Side Effects with Clinically Analogous Irradiation 4-1. Identifying of Radiation-Induced Pulmonary Fibrosis To identify an anti-pulmonary fibrosis effect according to a production of HSP27 dimers in a small animal model on lung side effects with clinically analogous irradiation, the small animal model was exposed to a radiation dose in a range of high dose clinical radiotherapy to induce a pulmonary fibrosis process.

Figure 4:
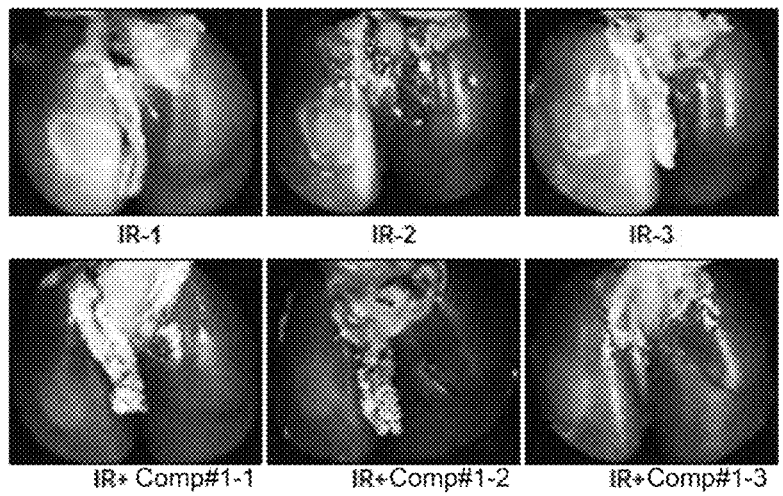
FIG. 4 shows results of identifying a degree of pulmonary fibrosis progress according to a production of altered HSP27 dimers in an animal model.
Figure 4:
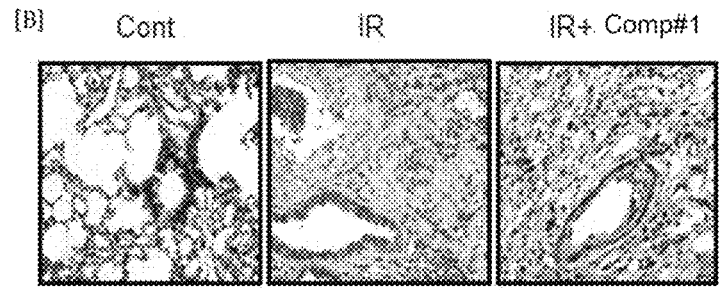
Figure 4:
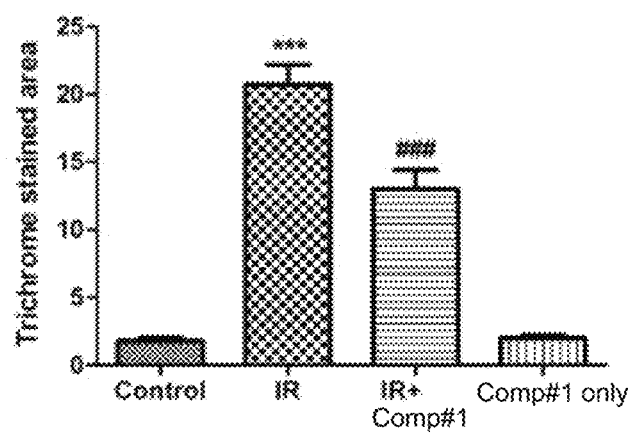

As shown in FIG. 4(A), a 10 week-old C57BL/6 male mouse was anesthetized with an anesthetic mixture of 30 mg/kg Zoletil and 10 mg/kg Rompun, after which a left lung of the mouse was exposed to a high dose radiation of 75 Gy in a 3 mm range by using X-Rad 320 (Precision, North Branford, Conn., USA). Then, Compound 1 of the present invention was intraperitoneally administered to the mouse at a 13.6 mg/kg concentration three times a week. During its sacrifice, the mouse was anesthetized, after which 10% formalin was injected into the anesthetized mouse through an airway thereof to fix its lung, such that a tissue sample was prepared by using a paraffin embedding.

In result, as shown in FIG. 4(B), it was identified that an immune response lesion occurred to a locally irradiated region, but it could be also identified with the naked eye that the lesion was recovered from a lung of a group, in which Compound 1 of the present invention was administered to produce altered HSP27 dimers.

Thus, it can be identified that the compound of the present invention has an effect on prevention or treatment of pulmonary fibrosis.

4-2. Identifying of a Degree of Collagen Accumulation

An amount of collagen was histologically identified through Masson's trichrome dyeing to compare degrees of pulmonary fibrosis with each other.

In result, as shown in FIG. 4(C), it was observed that a more amount of collagen was accumulated in an irradiated region of a locally irradiated mouse, and it could be also identified that an amount of collagen accumulation was decreased in a mouse, which was locally irradiated and administered with the compound of the present invention.

Based on the above results, it can be seen that chromenone derivatives, the compound of the present invention, have an inhibitory effect on pulmonary fibrosis.

What is claimed is:

1. A method for treating pulmonary fibrosis comprising administering a therapeutically effective amount of a chromenone derivative represented by Formula I or a pharmaceutically acceptable salt thereof to a patient in need thereof:

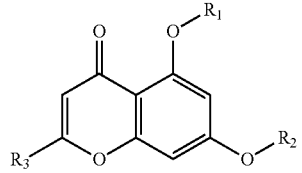

[Formula I]

wherein $R_1$ is hydrogen,

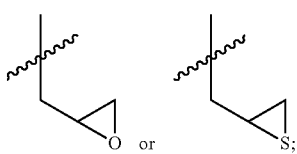

R₂ is

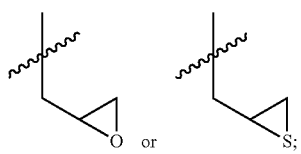 [SMILES: *CC1CO1 ; *CC1CS1]

and

R₃ is methyl or phenyl.

2. The method of claim 1, wherein the pulmonary fibrosis is one or more selected from the group consisting of idiopathic pulmonary fibrosis, pulmonary fibrosis resulting from anticancer therapy, middle east respiratory syndrome (MERS) or pneumonia.

3. The method of claim 2, wherein the anticancer therapy is radiotherapy.

4. The method of claim 1, wherein the chromenone derivative represented by Formula I or pharmaceutically acceptable salt thereof induces altered dimerization of heat shock protein 27 (HSP27), thereby inhibiting chaperone function.

5. The method of claim 1, wherein the chromenone derivative represented by the formula I is selected from the group consisting of following compounds:

| Compound | Structure |
|---|---|
| 1 | |
| 2 | |
| 3 | 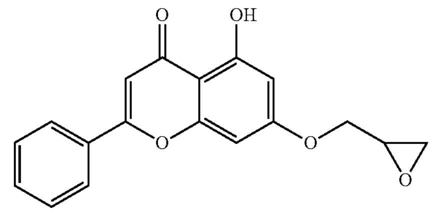 [SMILES: O=c1cc(-c2ccccc2)oc2cc(OCC3CO3)cc(O)c12] |
| 4 | 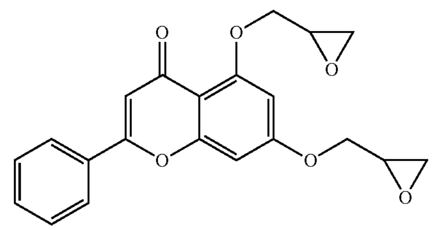 [SMILES: O=c1cc(-c2ccccc2)oc2cc(OCC3CO3)cc(OCC3CO3)c12] |
| 5 | 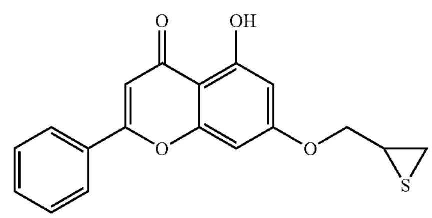 [SMILES: O=c1cc(-c2ccccc2)oc2cc(OCC3CS3)cc(O)c12] |
| 6 | 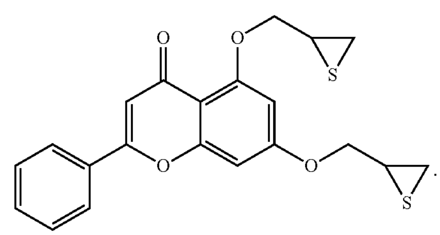 [SMILES: O=c1cc(-c2ccccc2)oc2cc(OCC3CS3)cc(OCC3CS3)c12] |

* * * * *